(12) United States Patent
Pai et al.

(10) Patent No.: US 7,865,010 B2
(45) Date of Patent: Jan. 4, 2011

(54) WAFER EDGE INSPECTION AND METROLOGY

(75) Inventors: Ajay Pai, Crystal, MN (US); Tuan D. Le, Minneapolis, MN (US)

(73) Assignee: Rudolph Technologies, Inc., Flanders, NJ (US)

( * ) Notice: Subject to any disclaimer, the term of this patent is extended or adjusted under 35 U.S.C. 154(b) by 0 days.

(21) Appl. No.: 12/571,801

(22) Filed: Oct. 1, 2009

(65) Prior Publication Data

US 2010/0086197 A1    Apr. 8, 2010

Related U.S. Application Data

(63) Continuation of application No. 11/525,530, filed on Sep. 22, 2006, now Pat. No. 7,616,804.

(60) Provisional application No. 60/830,015, filed on Jul. 11, 2006.

(51) Int. Cl.
*G06K 9/00* (2006.01)
(52) U.S. Cl. .................... 382/145; 382/199; 382/232
(58) Field of Classification Search ................ 382/145, 382/199, 232
See application file for complete search history.

(56) References Cited

U.S. PATENT DOCUMENTS

| | | | |
|---|---|---|---|
| 5,748,804 A * | 5/1998 | Surka | 382/291 |
| 6,522,777 B1 | 2/2003 | Paulsen et al. | |
| 6,714,679 B1 * | 3/2004 | Scola et al. | 382/199 |
| 7,197,178 B2 * | 3/2007 | Simpkins | 382/145 |
| 2002/0181762 A1 * | 12/2002 | Silber | 382/154 |
| 2002/0191832 A1 | 12/2002 | Guest et al. | |
| 2005/0013476 A1 | 1/2005 | Simpkins | |
| 2005/0036671 A1 * | 2/2005 | Watkins et al. | 382/145 |

OTHER PUBLICATIONS

Leica Microsystems product brochure entitled "LEICA LDS3300—The Integrated Solution for Automated Macro & Micro Defect Detection, Classification & High Resolution Review," © Germany 2005; 8 pgs.
PCT Search Report (mailed Sep. 12, 2008); 11 pgs.

* cited by examiner

*Primary Examiner*—Bhavesh M Mehta
*Assistant Examiner*—Stephen R Koziol
(74) *Attorney, Agent, or Firm*—Dicke, Billig & Czaja, PLLC

(57) ABSTRACT

Some aspects of the present invention relate to a wafer inspection method. A plurality of images is acquired about an edge portion of a wafer. Each of the images comprises a pixel array having a first dimension and a second dimension. A composite image of compressed pixel arrays is generated by compressing each of the pixel arrays in the first dimension and concatenating the pixel arrays. The composite image is analyzed to identify a wafer feature, for example using a sinusoidal line fit.

7 Claims, 8 Drawing Sheets

WAFER EDGE INSPECTION AND METROLOGY

CROSS-REFERENCE TO RELATED APPLICATION

This patent application is a continuation of U.S. patent application Ser. No. 11/525,530, entitled "WAFER EDGE INSPECTION AND METROLOGY", having a filing date of Sep. 22, 2006, which claims priority under 35 U.S.C. §119(e) to U.S. Provisional Patent Application Ser. No. 60/830,015, entitled "WAFER EDGE INSPECTION AND METROLOGY," having a filing date of Jul. 11, 2006.

This patent application is related to U.S. patent application Ser. No. 10/890,933, entitled "PHOTORESIST EDGE BEAD REMOVAL MEASUREMENT," having a filing date of Jul. 14, 2004, the contents of which are incorporated herein by reference.

BACKGROUND OF THE INVENTION

Over the past several decades, semiconductor-driven technologies have grown exponentially and have revolutionized our society. Manufacturers of semiconductors have made vast improvements in production, resulting in improved end product quality, speed, and performance. However, there continues to be demand for faster, more reliable, and higher performing semiconductors. To assist with these demands, better inspection systems and methods are continuously being sought.

For reference, semiconductors are often manufactured in wafer format, with each wafer including a series of layers, including, for example, a silicon and insulator layer or layers in a silicon-on-insulator or SOI wafer. Regardless, during wafer production, masking layers or resist layers are often times applied to a wafer in order to facilitate wafer patterning. Typically, a desired amount of liquid resist is applied to a top surface of a wafer while the wafer is being rotated. As the wafer is rotated, the resist material spreads outward radially from the center of the wafer and toward the semiconductor edge such that the wafer is substantially coated with a circular layer of resist. Excess amounts of resist can accumulate and form a mound or bead of resist toward an outer edge of the semiconductor wafer. At times, the resist also flows over the wafer edge, which can contaminate an edge normal and a backside of the wafer. Various edge bead removal (EBR) processes are applied in order to eliminate the "edge bead" of resist and/or other unwanted material proximate the wafer edge.

It is also noted that during wafer production, various material removal processes are employed, including, for example, wet etches, a dry etches, polishing, chemical mechanical polishing (CMP), and others depending on the materials being removed. During EBR removal, for example, chemical EBR units remove a ring of resist and other unwanted material about the edge of the wafer by dispensing a solvent referred to as EBR fluid, onto the resist of the semiconductor wafer. The solvent dissolves or develops away the resist and allows for easy removal of the resist from the edge of the semiconductor wafer. Wafer edge exposure (WEE) units can be additionally or alternatively applied for EBR purposes. WEE utilizes an optical unit to expose a ring of resist at or near the edge of the semiconductor wafer to light. During subsequent development processes, the exposed ring of resist is removed.

Variability or other problems with material removal processes, for example, can give rise to various concerns. For example, if the wafer is not centered during EBR, the ring of resist removed from the wafer edge will not be centered relative to the wafer. Thus, the remaining layer of resist will be offset on the wafer. This can result in defects in the integrated circuit devices formed proximate the wafer edges, for example. As another example, unevenly stacked substrate layers can result due to such offset, with substrate layer material being lifted and detrimentally re-deposited onto the semiconductor wafer. The re-deposited substrate material can contaminate the semiconductor wafer and cause defects in the integrated circuit devices formed on the wafer.

SUMMARY OF THE INVENTION

Some aspects of the present invention relate to wafer edge inspection systems and methods. According to some embodiments, a plurality of images are acquired about an edge of a wafer. Each of the images comprises a pixel array having a first dimension and a second dimension. A composite image of compressed pixel arrays is generated by compressing each of the pixel arrays in the first dimension and concatenating the pixel arrays. The composite image is analyzed to evaluate a wafer feature, for example by finding a location of the wafer feature or determining another characteristic of the wafer feature using a sinusoidal line fitting operation. Related products, systems, and methods are also contemplated and provided for in the description that follows.

DETAILED DESCRIPTION OF THE INVENTION

Figure 1:
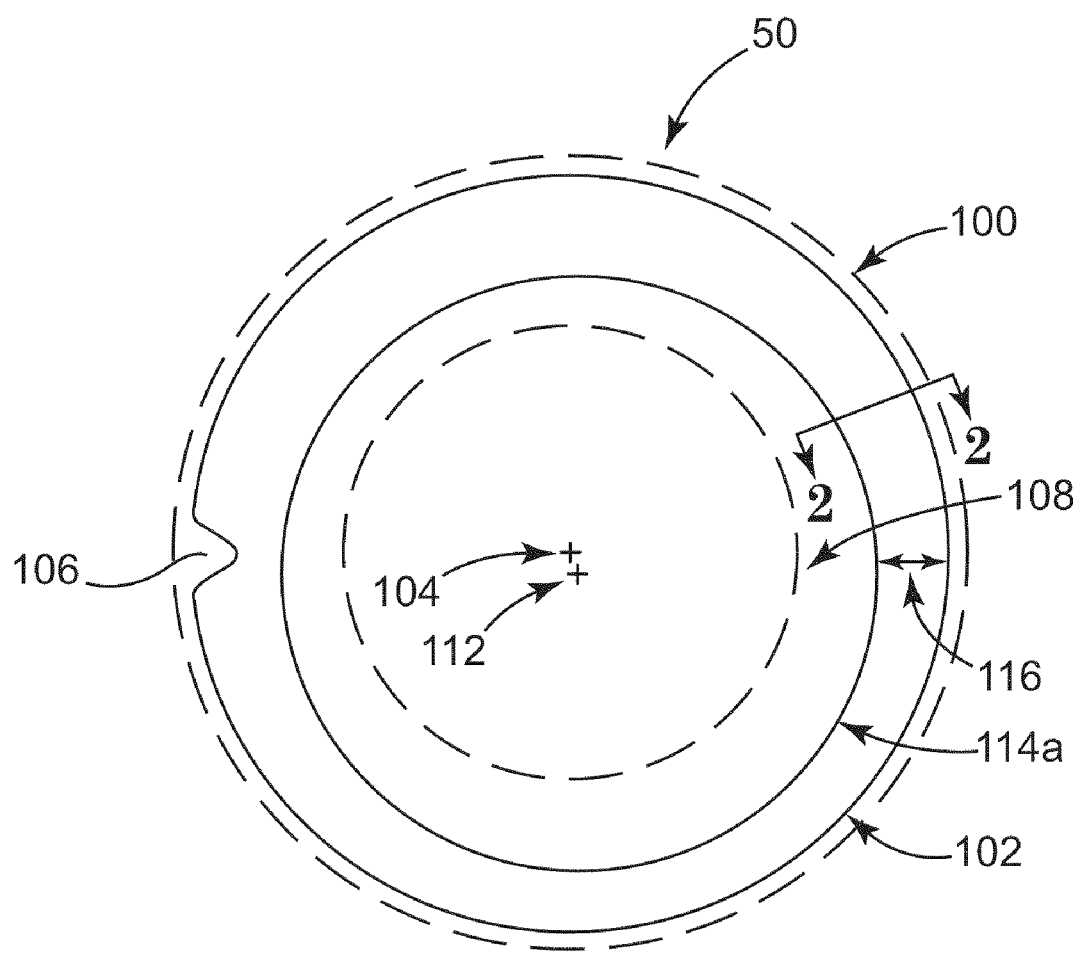
FIG. 1 is a schematic, top view of a wafer in accordance with principles of the present invention.

In general terms, wafer edge inspection systems and methods in accordance with principles of the present invention obtain edge image data from top, normal, and/or bottom directions in order to identify or locate various wafer features, including, but not limited to, wafer features proximate the wafer edge (such as wafer notch locations; various film layer edge locations, such as resist edge locations, insulator and/or silicon layer edge locations, or other locations; layer thicknesses, such as resist thickness or silicon layer thicknesses, wafer edge locations, resist edge to wafer edge offsets, edge bevel geometries and locations; and others) as well as other wafer features (such as wafer centers, resist layer centers, and wafer center to resist center offsets; and others), using data collected from edge imaging.

The characteristics of wafer features, including those described above, are often affected by material removal processes employed during wafer production. Thus, in some embodiments, evaluation/inspection of such features, including feature location, metrology, and/or other characterization is used to control such processes, for quality control, and/or to improve yields, for example. Some embodiment wafer edge inspection systems and methods are useful for measuring a wafer feature known as an edge bead removal line, or EBR line. For reference, an "EBR line" is indicative of a resist edge formed during an EBR process. Though the terms "resist edge," "edge of the resist," "edge bead removal lines," or "EBR lines" are generally used interchangeably herein, it should be understood that principles of the present invention apply to resist edges and other wafer features formed via a variety of wafer fabrication processes, inclusive of, but not limited to, edge bead removal (EBR) processes. Regardless, in some embodiments, wafer edge inspection systems and methods help better ensure that wafer processing is proceedingly correctly. For example, some embodiments include measuring EBR line position relative to a center of a wafer and/or relative to an edge of the wafer to provide information relating to whether the wafer is being properly centered during EBR processes and/or resist deposition processes.

As a part of inspecting various wafer features, some embodiment edge inspection systems and methods include acquiring a series of digital images about an edge portion of a wafer, for example with and associated sensor, such as an optical camera, positioned at a radial offset from a center of a rotating stage assembly. In some embodiments, an entire outer circumference of the wafer is imaged in a continuous and/or stepwise fashion. Edge images are compressed and evaluated cumulatively, for example via concatenation into a composite image, in order to characterize various wafer features such as those described above. For example, the distance from the edge of the wafer to a resist edge, such as an EBR line, is optionally evaluated about an entire circumference of the wafer. Any number of resist layers can be present on the wafer, each resist layer defining a resist edge. Thus, where applicable, each of a plurality of resist edges of interest is located as desired.

Additionally, it is contemplated that information obtained by imaging the wafer edge, such as a computed wafer center location, wafer edge location, the locations of resist edges, and/or others can be used in related inspection processes and systems. For example, wafer center location can be used for reporting and analyzing wafer defects. Wafer edge location is optionally used to help an inspection camera positioned to image a profile or side of the wafer edge ("normal edge") to track the normal edge and permit the camera to maintain proper focal distance from the normal edge of the wafer. Thus, in some embodiments, information collected with the edge inspection systems and methods is used as part of a larger, more detailed wafer characterization system or inspection methodology.

With reference to the figures, FIG. 1 illustrates a top view of a semiconductor wafer 50. The wafer 50 defines a top edge region 100 extending annularly about the wafer 50. The wafer 50 also includes a wafer edge 102, a wafer center 104, a wafer notch 106, a layer of resist 108, a resist center 112, a first resist edge 114a, for example a first EBR line, a second resist edge 114b (FIG. 8B), for example a second EBR line, and a distance 116 between the wafer edge 102 and the first resist edge 114a. The top edge region 100 extends from a portion of the layer of resist 108 proximate the first resist edge 114 to beyond the wafer edge 102 about the circumference of the wafer 50. In some embodiments, both the wafer 50 and the layer of resist are highly circular in shape.

FIG. 1 illustrates the resist center 112 at offset from the wafer center 104. This type of inconsistency can arise due to operator or mechanical error during formation of the resist 108 and/or removal of portions the resist 108. As previously alluded to, a location of a center of rotation of wafer 50 during fabrication affects the location of resist 108 relative to the wafer center 104, which, in turn, varies the distance 116 between the wafer edge 102 and the resist edge 114 about the top edge region 100. For example, in some embodiments, during various automated fabrication steps the wafer 50 is secured on a chuck, or stage assembly. However, due to automation or other errors, a center of rotation of the wafer 50 is misaligned from the wafer center 104. When the relative center of rotation is not aligned with the wafer center 104, resist or other layers are often eccentrically positioned relative to the wafer center 104 and the wafer edge 102.

FIG. 1 illustrates resist center 112 at an exaggerated offset from the wafer center 104, such that the misalignment between the two centers 104, 112 as well as non-uniformity of the distance 116 between the wafer edge 102 and the first resist edge 114a is readily discernable. However, in practice, misalignment (i.e., deviation from a desired degree of alignment) between centers 104, 112 and edges 102, 114 is often difficult to observe with the naked human eye.

Figure 2:
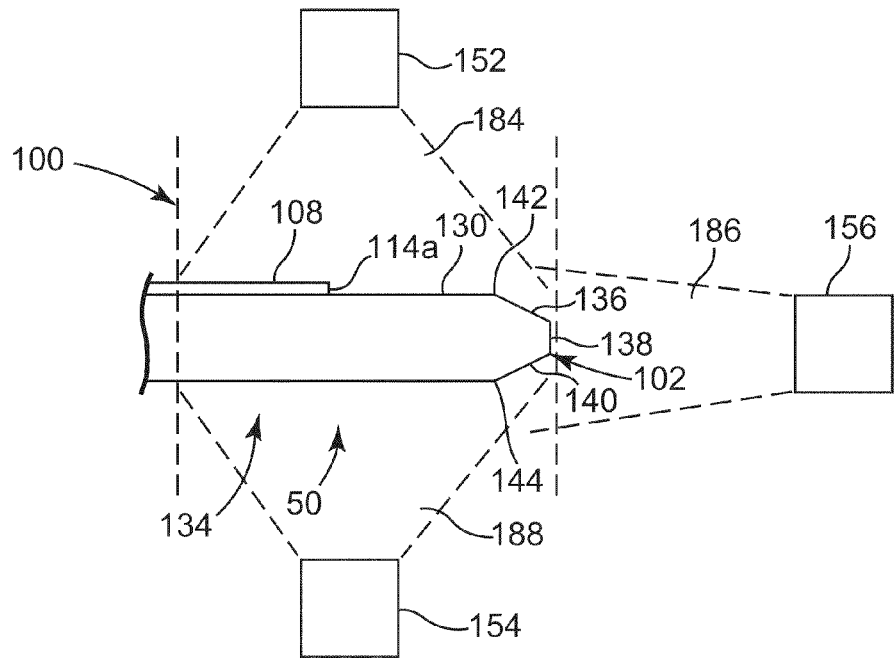
FIG. 2 is a schematic, sectional view of the wafer of FIG. 1 along line 2-2 and a portion of an associated edge inspection system in accordance with principles of the present invention.

FIG. 2 is a sectional view of the wafer 50 along line 2-2 as indicated in FIG. 1. The top edge region 100 includes the wafer edge 102, the first resist edge 114, and an exposed edge region 130 which is substantially free of the resist 108 and/or other unwanted surface materials. With reference between FIGS. 1 and 2, in some embodiments, the top edge region 100 is substantially annular in shape defining an inner diameter substantially inset from various edge features of interest, such as inset from an edge of the exposed region 130 and/or the resist edge 114a. Also shown is a bottom edge region 134 opposite the top edge region 100 which can also be substantially free of resist or other film layers and is optionally a mirror image of the top edge region 100 being defined by about the same boundaries. In some embodiments, the wafer 50 is beveled proximate the wafer edge 102 and defines a top bevel 136, a wafer edge normal 138, and a bottom bevel 140. The top bevel 136 has an origin 142 and extends to the wafer edge normal 138. The wafer edge normal 138 can generally be described as an outer face and boundary of the wafer 50, thus defining a location of the wafer edge 102. In turn, the bottom bevel 140 defines an origin 144 and extends to the wafer edge normal 138.

Figure 3:
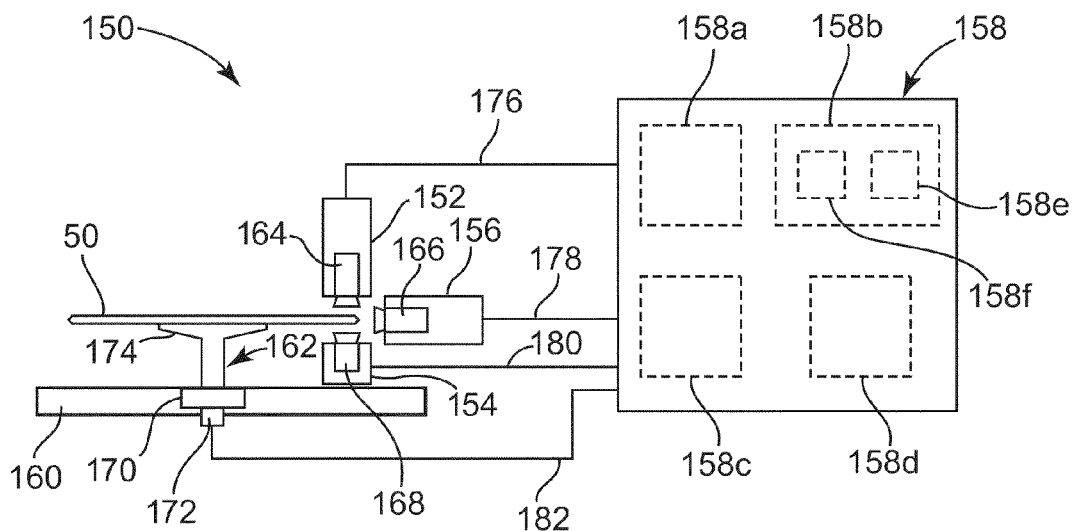
FIG. 3 is a schematic view illustrating the wafer of FIG. 1 and the edge inspection system of FIG. 2 in more detail in accordance with principles of the present invention.

FIG. 2 also illustrates a portion of an edge inspection system 150 according to some embodiments of the present invention, with FIG. 3 showing a more inclusive schematic of the edge inspection system 150. With reference between FIGS. 2 and 3, the edge inspection system 150 includes a top edge sensor 152, a bottom edge sensor 154, an edge normal sensor 156, a controller 158, a base 160, and a stage assembly 162.

The controller 158 includes various modules, such as program modules for operating the edge inspection system 150. In some embodiments, the controller 158 includes an image acquisition module 158a for receiving image data from one or more of the edge sensors 152, 154, 156, a composite image module 158b for generating a composite image of compressed images, an image analysis module 158c for analyzing the composite image to identify one or more wafer features, and a user interface module 158d for displaying the composite image 300 and/or other information to a user. The composite image module 158b further includes an image concatenating module 158e for stitching the images and an image compression module 158f for compressing the images. The system 20, including the various modules 158a to 158f of the controller 158, is adapted to perform edge inspection and evaluation of wafer features according to various embodiment methods of edge inspection described below.

The top edge sensor 152 includes a camera 164, the edge normal sensor 156 includes a camera 166, and the bottom edge sensor 154 includes a camera 168. The stage assembly 162 includes a motor 170, an encoder 172, and a support plate 174. The motor 170 is coupled to the encoder 172 and the support plate 174, such that the motor 170 is adapted to rotate the support plate 174. The encoder 172 provides counts for controlling the position of motor 170 (and thus the support plate 174), although other methods/apparatuses for controlling a position of the motor 170 are contemplated. The various sensors 152, 154, and/or 156 are generally adapted to capture images of the wafer 50, such as grayscale and/or color image data for example. Additionally, it should be understood that it is contemplated that the sensors 152, 154, 156 optionally operate according to a variety of principles or categories thereof, including for example, optical imaging, x-ray imaging, interferometric, Shack-Hartmann wavefront, and/or confocal principles in some embodiments.

The support plate 174 supports the wafer 50 during rotation and imaging of the wafer 50. The controller 158 is electrically coupled to the top edge sensor 152 through the communication link 176, to the edge normal sensor 156 through the communication link 178, to the bottom edge sensor 154 through the communication link 180, and to the stage assembly 162 through the communication link 182. The controller 158 controls the top edge sensor 152, the edge normal sensor 156, the bottom edge sensor 154, and the stage assembly 162 through the communication links 176, 178, 180, 182 for inspection of the top edge region 100, the bottom edge region 134, and/or the edge normal 138.

In particular, in some embodiments, the wafer 50 is inspected with the edge inspection system 150 from top, normal, and/or bottom directions, with various angles of inspection contemplated. In general terms, the edge inspection system 150 performs "top-down" inspection of the top edge region 100 (FIG. 2) via the top edge sensor 152. The edge inspection system 150 additionally or alternately performs "bottom-up" inspection of the bottom edge region 134 proximate via the bottom edge sensor 154 and/or the wafer edge normal 138 via the edge normal sensor 156. In some embodiments the edge inspection system 150 inspects an edge portion of the wafer 50, the edge portion including one or more of the top edge region 130, the bottom edge region 134, and/or the wafer edge normal 138 by acquiring image data at a plurality of circumferential image frame locations about the wafer 50. For example, the first resist edge 114, the exposed edge region 130, the top bevel 136, and the wafer edge 102 are all optionally imaged about the wafer 50 with the top edge sensor 152. In turn, the bottom edge sensor 154 and/or the edge normal sensor 156 are optionally used to image the bottom edge region 134 and edge normal 138, respectively about the entire wafer 50 or a portion thereof.

In particular, with reference to FIG. 2, the top edge sensor 152 has an inspection area 184, the edge normal sensor 156 has an inspection area 186, and edge bottom sensor 154 has an inspection area 188. In some embodiments, the edge inspection system 150 inspects the top edge region 100 of the wafer 50 including the first resist edge 114, the exposed edge region 130, and the top bevel 136; the edge normal 138; and the bottom edge region 134 including the bottom bevel 140, according to the inspection areas 184, 186, 188, respectively. It should be understood that, in some embodiments, the top edge region 100 generally corresponds to the inspection area 184. Brightfield illumination is used in some embodiments, although darkfield illumination, combinations of darkfield and brightfield illumination, and other imaging techniques such as those previously referenced are also contemplated.

Figure 4:
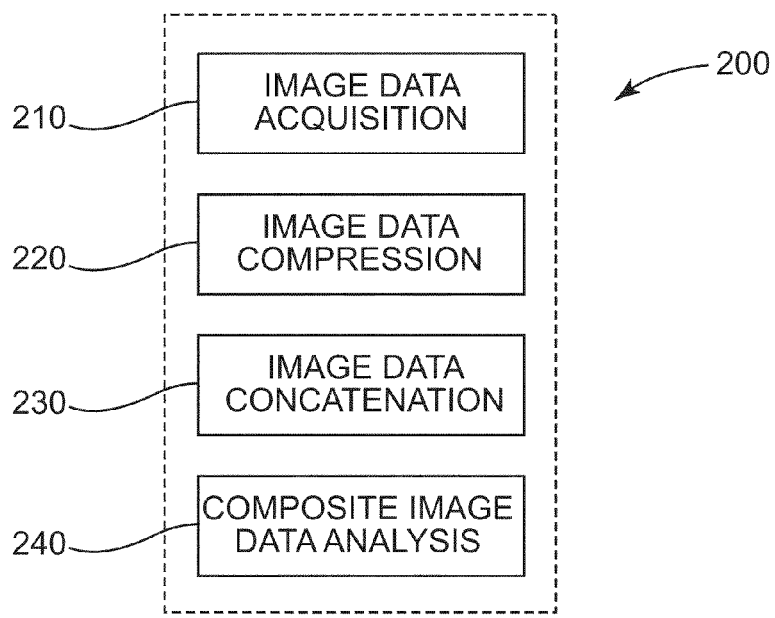
FIG. 4 is related to methods of edge inspection in accordance with principles of the present invention.

With reference to FIG. 4, some embodiments of a method of Wafer Edge Inspection 200 include Image Data Acquisition 210, Image Data Compression 220, Image Data Concatenation 230, and Composite Image Data Analysis 240, for example using the edge inspection system 150 (FIG. 3), including the various modules of the controller 158. With reference between FIGS. 2 and 3, although some embodiments of Wafer Edge Inspection 200 are described in association with imaging of the wafer top edge region 100, it should be understood that similar principles are applicable to characterize wafer features evaluated by imaging with the bottom of the wafer 50, such as features associated with the bottom edge region 134, and/or features associated with the wafer edge normal 138, for example. Thus, in some embodiments, similar data/processes are undertaken to those described below using the bottom edge sensor 154 to image and characterize wafer features associated with the bottom edge region 134 and/or using the edge normal sensor 156 to image and characterize wafer features associated with the wafer edge normal 138.

Figure 5:
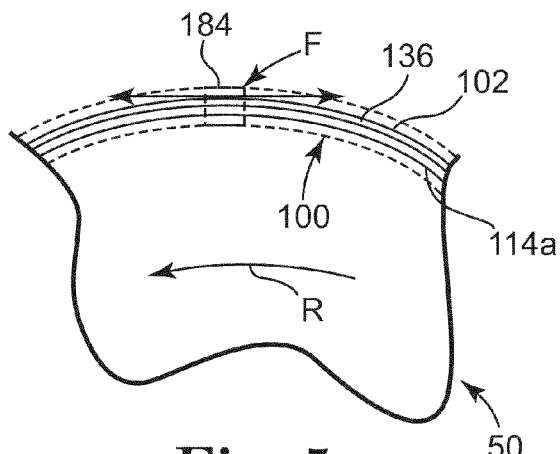
FIG. 5 illustrates the wafer of FIG. 1 during an edge inspection in accordance with principles of the present invention.

With the above in mind, and with reference to FIG. 5, in some embodiments Image Data Acquisition 210 includes using the edge inspection system 150 (FIG. 3) to acquire image data in the form of a plurality of images taken about the wafer top edge region 100 or other edge portion of the wafer 50, with each of the plurality of images being acquired about the wafer 50. The top edge sensor 152 (FIG. 3) images the top edge region 100 in the inspection area 184 with the wafer 50 being substantially continuously rotated, for example in rotational direction R, such that images are acquired circumferentially about the wafer 50. Such images are optionally acquired substantially continuously, for example using a line scan camera such as a TDI camera. In some embodiments, the wafer 50 can also be rotated in a step-wise fashion. Alternatively, or additional, a strobe light or other appropriate means is optionally utilized to obtain images in a step-wise fashion while substantially continuously rotating the wafer 50. Other variations on continuous/step-wise image acquisition should be apparent in view of the foregoing. As referenced above, images of the bottom edge region 134 and/or edge normal 138 are alternately or additionally acquired about the wafer 50. In some embodiments, the images are typically taken about an entirety of the circumference of the wafer 50, although images may also be taken partially about the wafer 50. Furthermore, in some embodiments, images are taken with some overlap in order to help ensure complete imaging or to otherwise increase image data resolution. However, non-overlapping images, separated images, and combinations thereof are also contemplated.

It should also be understood that the larger the wafer 50, the more images that will be required to image the wafer top edge region 100 or other region at a particular resolution. For example, a 300 mm diameter wafer is in comparison to a 200 mm diameter wafer will require a larger number of digital images to fully image the top edge region 100 about the circumference of the wafer 50. Similarly, if a smaller wafer is used, such as 100 mm wafer, a smaller number of digital images are required to fully image the top edge region 100, for example, about the circumference of the wafer 50. Thus, various combinations of magnifications (e.g., a smaller, higher resolution inspection area 184), wafer diameters, and numbers of images taken about the top edge region 100 are also contemplated. In some embodiments, for a 200 mm wafer configuration, 128 digital images are acquired to help ensure substantially 360 degree coverage of images of the top edge region 100 or edge portion of the wafer 50, such as the bottom edge region 134 or edge normal 138. However, the top edge inspection sensor 152 optionally acquires more numerous or less numerous images as desired, such as up to about 360 images or more. In some embodiments, the top edge inspection sensor 152, for example, has a resolution of up to about 7 micrometers, although other resolutions including both higher and lower resolutions, are also contemplated.

One, two, or any number of full passes around the wafer 50 can be completed with image data collected as desired at the various image frame locations. In some embodiments with two passes, the first pass is brightfield data, while the second pass is darkfield data. If desired, the wafer 50 is "over turned" or spun more than a single revolution in association with each "full pass." For example, the wafer 50 is optionally spun 1.1 revolutions or 1.2 revolutions. As another example, the wafer 50 is optionally "over turned" more than 2 revolutions, such as 2.1 revolutions or 2.2 revolutions. Such "over turning" is optionally used in order to help ensure some overlap at a beginning and end of image acquisition, or to otherwise secure a desired amount of image information. It should also be understood that any number or fraction of additional/fewer passes are taken around the wafer 50 as desired.

Figure 6A:
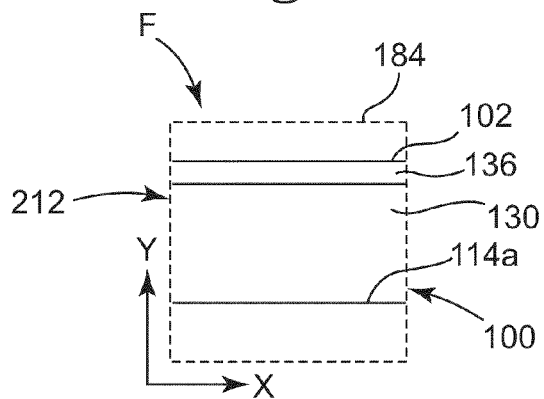
FIG. 6A is a schematic view of an image of a top edge region acquired during edge inspection in accordance with principles of the present invention.
Figure 6B:
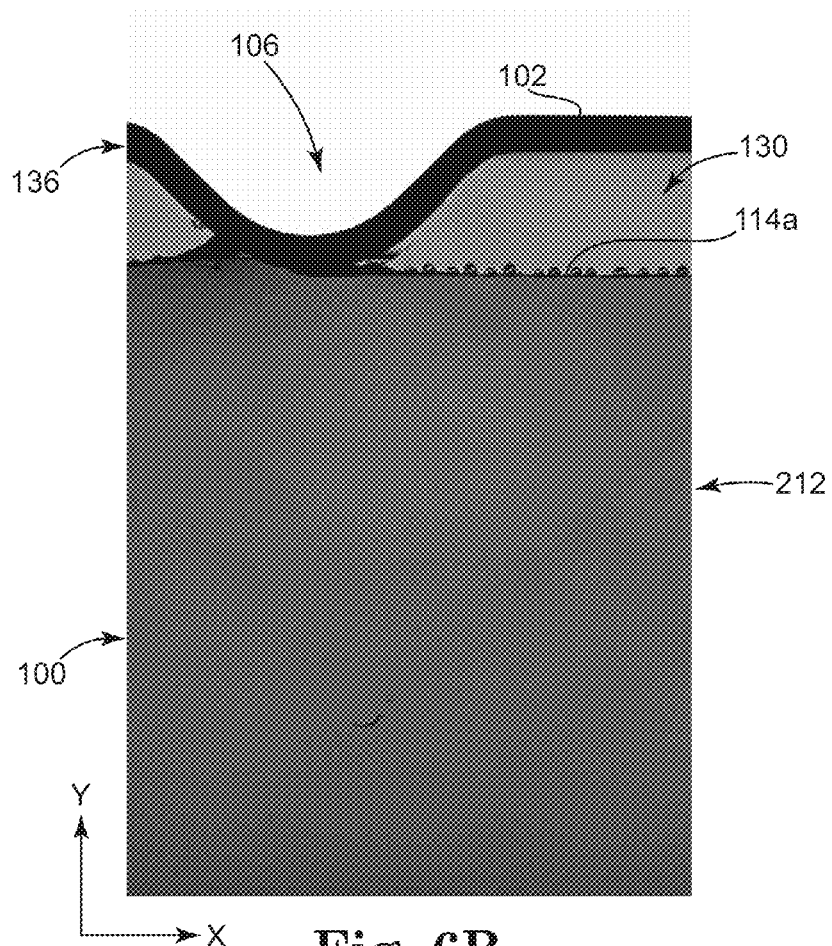
FIG. 6B is an example of an image of a top edge region showing a wafer notch in accordance with principles of the present invention.

FIG. 6A is a generalized, schematic representation of a first image of the plurality of images taken at a first frame acquisition location F during Image Data Acquisition 210 according to some embodiments. For additional reference, FIG. 6B is one example of an image of the top edge region 100 acquired according to related embodiments of the present invention, FIG. 6B also showing the notch 106. Returning to FIG. 6A, each of the plurality of images comprises a pixel array, with the first image comprising a first pixel array 212. The pixel array 212 is described in more detail to illustrate principles that are applicable to each of the plurality of pixel arrays associated with the plurality of images. In general terms, the pixel array 212 comprises a plurality of pixels arranged in an array, with the pixel array 212 having a first dimension X and a second dimension Y. Each pixel of the pixel array 212 has an associated pixel characteristic value, such as a brightness value, with wafer features, such as the first resist edge 114, the exposed edge region 130, the first resist edge 114, the top bevel 136 the bottom edge region 134, and wafer edge normal 138 causing variations in the pixel characteristic values.

Pixel characteristics optionally include grayscale brightness information, although other types of information, color data, for example, are also contemplated. For example, some embodiments include using a filter or other means to acquire red, blue, and/or green light intensity image data. Additionally or alternatively, combinations of grayscale and color data, such as red, blue, and/or green data is optionally acquired and analyzed, for example using a Bayer camera. Additionally, it is contemplated that a pixel characteristic value optionally corresponds to a height value of the pixel in some embodiments. From the above, it should be understood that a variety of types pixel characteristic values are contemplated, including those associated with any pixel characteristics that are representative of one or more wafer features.

In some embodiments, the first dimension X of the pixel array 212 is substantially tangential to wafer 50, and in particular wafer edge 102, with the dimension Y being substantially radially aligned to the wafer 50, although other orientations of the pixel array 212 are also contemplated, or may result due to wafer offset during inspection, for example. In one embodiment, the pixel array 212 comprises an array of 1,600 horizontal pixels across the first dimension X by 1,200 vertical pixels across the second dimension Y (1,920,000 pixels), although other pixel arrays are contemplated. For example the pixel array 212 is optionally 1,920 pixels across the first dimension X by 1,078 pixels across the second dimension Y (2,069,760 pixels).

Image Data Compression 220 includes compressing the acquired images. In particular, the plurality of pixel arrays are each compressed in the first dimension X, resulting in a plurality of compressed pixel arrays. In some embodiments, compression of the pixel arrays results in the compressed pixel arrays being spaced apart from one another at their respective image frame locations about the wafer 50. In other words, unless there is an extreme amount of overlap and/or a relatively low amount of compression, there will be some "spacing" between the compressed pixel arrays according to their respective image frame locations. In some embodiments, image compression assists in removing or reducing image information relating to wafer patterning, random variations in image data, or other undesirable image information. Such patterns or other random variations can otherwise cause difficulties in finding the first resist edge 114a, as well as other wafer features.

In some embodiments, compression is achieved in first dimension X alone, with the second dimension Y remaining entirely "uncompressed" or "non-compressed." Regardless, compression, for example across the first dimension X, is accomplished via a variety of methods. For example, the pixel characteristic values of the pixel arrays are optionally averaged across the first dimension to get an average pixel characteristic value. In some embodiments, pixel array 212 is compressed by averaging the brightness values of the pixel array 212 across the first dimension X to generate a single column of pixel brightness values in the second dimension Y. In somewhat different terms, the plurality of acquired images are optionally compressed by average pixel rows, across the first dimension X, resulting in a multitude of images that are full depth in the second dimension Y, but only one pixel wide in the first dimension X. It is also contemplated that the pixel characteristic values of the pixel array 212 are optionally compressed to more than a single column of pixels or otherwise as desired.

Utilizing compression, pixel characteristic variations that are not of interest (such as random image variations or wafer patterning) across the first dimension X can be reduced to highlight variations from desired features, such as more regular features that extend along the first dimension X. Thus, image compression along the first dimension X can be used to perform noise and/or undesirable edge suppression, for example. In more conceptual terms, in some embodiments, image variations or aberrations that do not extend along the first dimension X are substantially reduced to bring out or otherwise highlight wafer features that more or less extend circumferentially about the wafer top edge region 100, although features extending in other directions/having other shapes can also be highlighted as desired. Thus, brightness variations, for example, in the pixel array 212 due to such features as the wafer edge 102 (FIG. 1), the first resist edge 114*a* (FIG. 1), the top bevel 136 (FIG. 2), a silicon or insulator layer edge (not shown), or the exposed edge region 130 (FIG. 2), can become more pronounced, or retain their relative strength(s). In turn, more random brightness variations, or features that do not substantially extend circumferentially about the wafer 50, such as die patterns (not shown) or test patterns (not shown) on the wafer 50, are filtered or become less pronounced. This can be particularly advantageous where wafer patterning crosses or otherwise interferes with an EBR line or other wafer feature to be located.

It should also be understood that image compression is optionally performed additionally or alternatively in another direction, not tangential to the wafer edge 102, in order to highlight and/or filter out a variety of other image artifacts or variations as described. Furthermore, similar image compression principles are applicable to images acquired of the wafer edge normal 138 and/or bottom edge region 134, for example. In some embodiments, where regular features on the wafer 50, e.g. streets, missing die, notches, flats or fiducials, undesirably show up in a compressed image, such features often will most likely have a recognizable signature. While these signatures may vary in terms of appearance, it is contemplated that they will tend to appear in a compressed image in predetermined locations related to their actual locations on the wafer 50. Accordingly, these signatures may be removed, either automatically or manually. In some embodiments, automatic removal of these signatures may involve the use of image recognition algorithms or techniques to identify and remove such signatures. Manual and/or automatic removal may involve, in some embodiments, selecting a regular feature to be removed from analysis, such as by defining a region of interest that surrounds the regular wafer feature and instructing the controller 158 to ignore image data from that region, and removing image data prior to image compression and/or following image compression as desired.

Although compressed images are optionally analyzed to locate or otherwise characterize various wafer features, in some embodiments, the wafer edge 102, the top edge bevel 136, and/or the first resist edge 114*a* are located using a best-circle-fit to the plurality of spaced-out, compressed pixel arrays. A location of the wafer center 104 and/or the resist center 112 can then be determined. In other words, one or more wafer features are optionally determined from "un-concatenated" or "non-concatenated" data according to image frame acquisition location. However, as described below, analysis of concatenated, composite image data is used in some embodiments in order to locate/identify one or more wafer features, as well as features associated with the bottom edge region 134 as desired.

Image Data Concatenation 230 optionally proceeds prior to or following image compression. However, concatenation of the compressed pixel arrays can be more efficient in some embodiments, as less data is operated upon in order to perform the concatenation (millions of pixels for each image being concatenated in comparison to thousands of pixels, for example).

FIG. 7A is a generalized, schematic illustration of the compressed pixel arrays acquired of the top edge region 100 (see also FIGS. 1, 2, and 3) concatenated into a composite image 300 having an associated first axis M and a second axis N. For reference, the terms "stitching" and "concatenating" are used interchangeably herein and generally refer to either aligning overlapping image data as well as aligning image data in an "edge-to-edge" fashion, as appropriate. As described in greater detail below, the composite image 300 is analyzed to locate or otherwise characterize one or more wafer features, such as the first resist edge 114*a*, the wafer edge 102, the top bevel 136, the wafer center 104 (FIG. 1), the resist center 112 (FIG. 1), or any other wafer features including others expressly or implicitly described herein.

In general terms, each of the plurality of compressed pixel arrays are aligned to one another in a sequential manner (e.g., according to an angular position of the image frame acquisition location at which they are taken about the wafer 50). Concatenation is performed using a concatenation algorithm, such as concatenation algorithms known to those of ordinary skill in the art. The concatenation algorithm or other concatenating program module is applied to the plurality of compressed pixel arrays in order to help ensure that the images are properly aligned. Thus, in some embodiments where the plurality of compressed pixel arrays have been compressed into a single column of pixels, the composite image 300 comprises each of the columns of pixels aligned as desired in a sequential manner according to the angular position of their respective image frame acquisition locations about the wafer 50.

As referenced above, the composite image 300 is "filtered" via the pixel array compression previously described such that wafer features which extend in a substantially circumferential manner about the wafer 50 are more readily identified via edge detection and region growing techniques, for example, as described in greater detail below. In some embodiments, the first and second axes M, N generally correspond to the first and second dimensions X, Y, respectively, of each of the compressed pixel arrays. The first axis M is described in angular units, such as 0 degrees to 360 degrees or −180 degrees to +180 degrees, for example, while the second axis N is described in units of distance, micrometers, for example.

Figure 7:
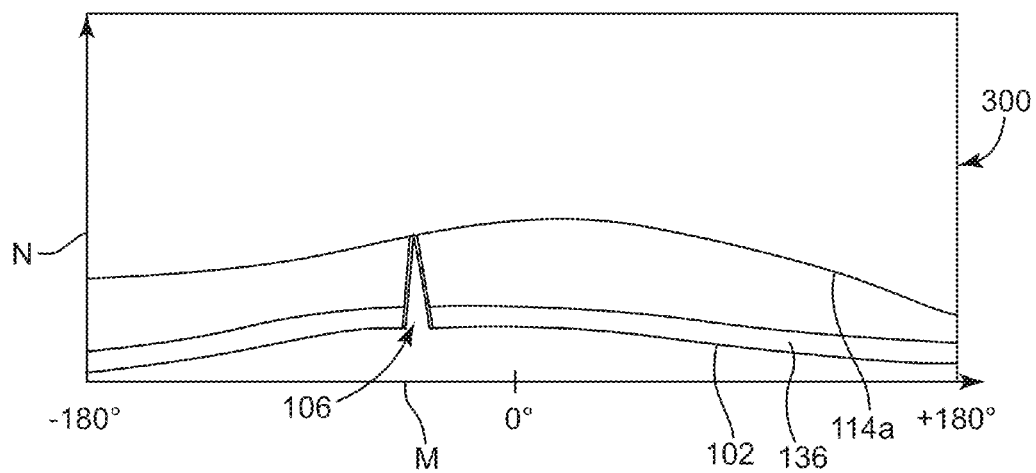
FIG. 7 is a schematic view of a composite image of compressed images in accordance with principles of the present invention.

With reference between FIGS. 1 and 7, where the wafer 50 is well-centered during imaging of the top edge region 100, for example, and in the absence of other imaging deviations, the wafer edge 102 should be represented in the composite image 300 as a substantially straight line. However, where alignment errors occur, for example, where the wafer 50 is offset to some extent on the stage assembly 162, the wafer edge 102 will take a more sinusoidal shape in the composite image 300 as indicated generally in FIG. 7. In other words, the offset of some embodiments induces eccentricity in the imaging of the wafer edge 102, which results in the wafer edge 102 taking a more sinusoidal shape due to the fact that the wafer edge 102 according to the circularity of the wafer edge 102.

In a similar manner, the first resist edge 114 is also shown in FIG. 7 to have a somewhat irregular, non-linear shape. Where the first resist edge 114 is at a substantially regular distance from the wafer edge 102, for example where the wafer center 104 and the resist center 112 are aligned well, the first resist edge 114 will track the wafer edge 102, the two having a substantially similar shape. In turn, where the first resist edge 114 varies in distance relative to the wafer edge 102, the shape of the wafer edge 102 and the resist edge 114 become more disparate, for example where the layer of resist 108 is not centered on the wafer 50. Thus, where the wafer center 104 is centered with the resist center 112, and the wafer 50 is centered on the stage assembly 162 (and in the absence of other imaging eccentricities, for example), both the wafer edge 102 and the first resist edge 114 will extend in a substantially linear manner within the composite image 300. Where the distance between the first resist edge 114 and the wafer edge 102 is substantially constant about the entire circumference of the wafer 50, but where the wafer 50 is not centered during imaging, for example, the wafer edge 102 and the first resist edge 114 will have more sinusoidal shapes, each of the sinusoids tracking well with one another. However, as variability between the first resist edge 114 and wafer edge 102 increases, the sinusoidal shapes of the wafer edge 102 and the shape of the first resist edge 114 will generally become more and more disparate.

Figure 8A:
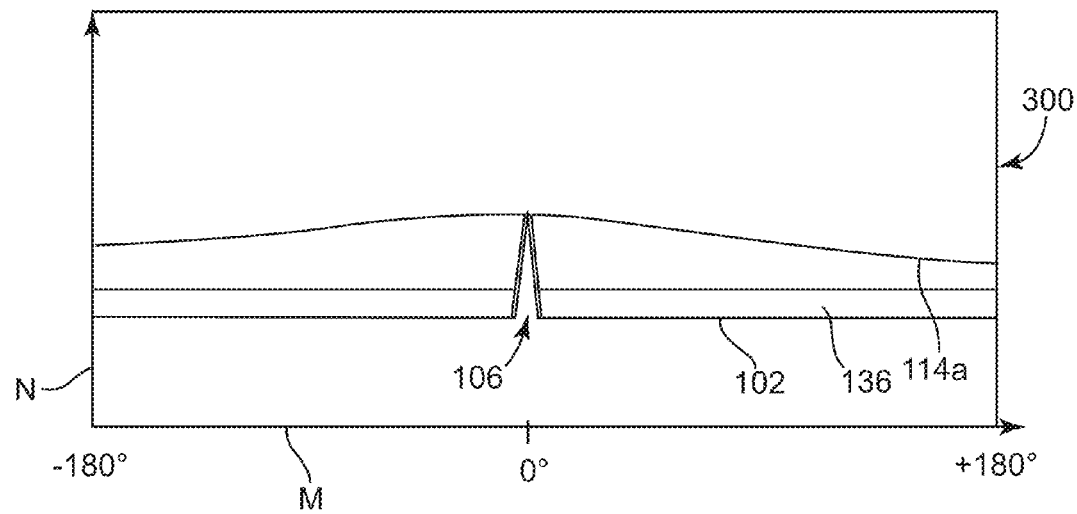
FIG. 8A is schematic a view of the composite image of FIG. 7 following normalization to a found wafer edge in accordance with principles of the present invention.
Figure 8B:
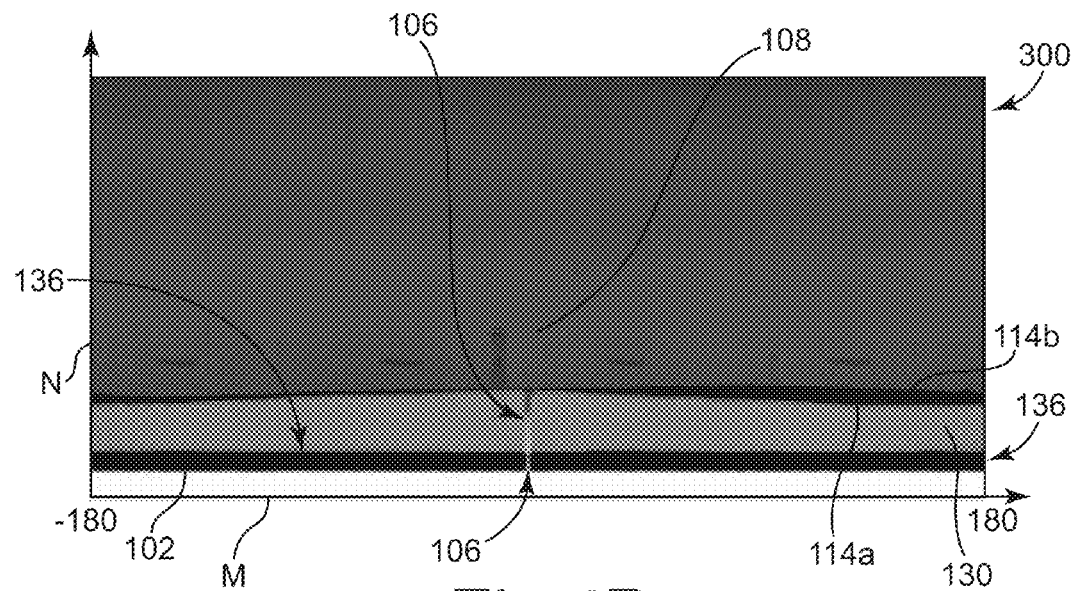
FIG. 8B is an example of a normalized composite image generated during an edge inspection in accordance with principles of the present invention.

With reference to the generalized, schematic view of FIG. 8A, in some embodiments, the composite image 300 of the top edge region 100, for example, is normalized to the wafer edge 102. FIG. 8B shows an example of the composite map 300 acquired according to some embodiments and normalized such that the wafer edge 102 is substantially straight. Of note, FIG. 8A shows the first resist edge 114a highlighted, while embodiments of the first and the second resist edges 114a, 114b are visible in FIG. 8B. Regardless, the wafer edge 102 is optionally located by applying one or more edge detectors to the non-concatenated compressed pixel arrays and applying a best-circle-fit. In other embodiments, the wafer edge 102 is located in the composite image 300 in a similar manner to the first resist edge 114, as described in greater detail below. Regardless, the composite image 300 is optionally normalized based on the found wafer edge 102, such that the composite image is shifted with the found wafer edge 102 being a straight line, although the composite image 300 can be normalized such that the wafer edge 102 takes on other shapes as desired. As described in greater detail below, in some embodiments, the composite image 300 or a composite image of another region of interest, such as the wafer edge normal 138, for example, is visually displayed to a user or others. Normalizing the composite image 300 to the found wafer edge 102 or other feature can assist a user in visualizing or otherwise understanding an amount of offset of the various wafer features, for example the distance 116 of the first resist edge 114a from the wafer edge 102. The composite image 300 of the top edge region 100 or a composite image relating to another imaged region, is displayed in a normalized form, for example following normalization of the wafer edge 102 as detected, and/or following transformation with one or more edge detectors, as will be described in greater detail.

If desired, the wafer notch 106 or a flat, which appears as a discontinuity in the composite image 300, is located and centered in the composite image 300 by shifting the first axis M, for example by "zeroing" the first axis M to the wafer notch 106 such that the wafer notch 106 is located at zero degrees on the first axis M. The ability to simply shift the composite image 300 on the first axis M such that the wafer notch 106 is at the zero degree position is due to the fact that the top edge region 100 is of a continuous, circular nature.

The notch 106 is optionally identified by applying one or more edge detectors and fitting two intersecting lines to edges corresponding to the edges of the notch 106, where the intersection represents a center of the wafer notch 106. In some embodiments, the notch 106 is detected using uncompressed images with notch location information obtained from the uncompressed images. However, in some embodiments, a location of the wafer notch 106 is optionally found using the composite image 300.

Figure 9:
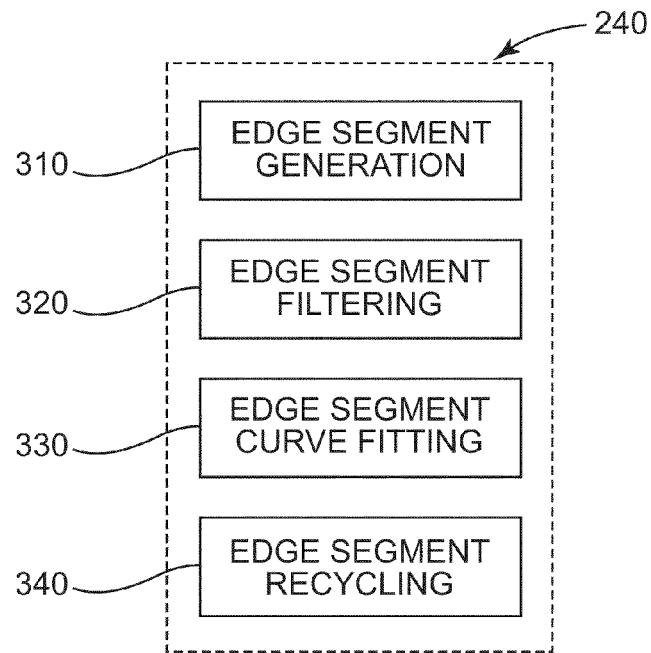
FIG. 9 relates to a method of the composite image data analysis of FIG. 4 in accordance with principles of the present invention.

With reference to FIG. 9, Composite Image Data Analysis 240 includes Edge Segment Generation 310, Edge Segment Filtering 320, Edge Segment Curve Fitting 330, and Edge Segment Recycling 340. Edge Segment Generation 310 includes applying one or more edge detectors to the composite image 300. In some embodiments, a Sobel edge detector and a Canny edge detector are applied to the composite image 300 to generate edge gradient data corresponding to the pixels making up the composite image 300. Upper and lower gradient thresholds, as well as other criteria, are set as desired either automatically or manually in order generate edge segment data or otherwise grow one or more edge segments corresponding to a feature to be located or otherwise characterized from the edge gradient data. For example, based on a starting pixel characteristic and edge threshold condition (contrast in some instances), edge segments are "grown" by adding pixels to a segment grouping if they meet the selected edge segment threshold conditions.

In some embodiments, Edge Segment Filtering 320 includes using edge segment intensity cross-section is analyzed to determine a profile of an edge segment, which can be indicative of a resist edge, such as the first resist edge 114a, and/or noise and allows bad edge segments to be discarded or prefiltered before or during curve fitting. If desired, a user is allowed to adjust upper and lower edge gradient thresholds, edge strength threshold (e.g., average edge segment edge gradient), and/or segment size thresholds (for example a minimum edge segment length) to disregard or highlight particular edge segments in order to facilitate wafer feature identification. It is also contemplated that the edge inspection system 150 automatically adjusts or selects such criteria in some embodiments. In this manner, edge segments are filtered to a particular size, edge strength, and/or minimum gradient value, or according to other criteria, prior to, Edge Segment Curve Fitting 330, although such filtering may alternatively or additionally occur during or after Edge Segment Curve Fitting 330.

Edge Segment Curve Fitting 330 includes identifying edge segments of a plurality of generated edge segments that correspond to a selected wafer feature. In some embodiments, Edge Segment Curve Fitting 330 includes selecting a first edge segment generated from the edge gradient and fitting a sinusoidal curve to the first edge segment. In particular, wafer features extending about the wafer 50, such as the first resist edge 114a, silicon or insulator layer edges (not shown), the bevels 136, 140, the wafer edge 102, and others are represented well by sinusoidal lines. This is at least partially attributable to the circular, including annular, shape of such wafer features. In particular, this result is understood with reference to the generally understood relationship between circles and sinusoids and that an eccentrically positioned EBR line will generally appear as a sinusoid in the composite image 300. Thus, based on an assumption that the first resist edge 114 is substantially circular, eccentricity between the wafer 50 and the layer of resist 108 results in a sinusoidal shape in the composite image 300. As such, sinusoidal curve fitting, for example using Least Squares optimization techniques, is applied to fit a first curve to the detected segments. However, other types of curves or line fitting are also contemplated for curve fitting the edge segments. For reference, it should be understood where the wafer feature to be located using sinusoidal curve fitting is substantially straight, a sinusoid having a small or substantially no amplitude will be fit to the feature to be located.

In some embodiments, one or more subsequent edge segments are identified and segment distance (average, median or and/or absolute) from the first sinusoidal curve fit is calculated to see if subsequent segments are a good fit with the first fit curve. Where a subsequent segment is a good fit, that segment is grouped, merged, concatenated, or the like, with a first group of segments and a subsequent, second sinusoidal curve is fit to the new first group of edge segments. In some embodiments, this process continues iteratively until a potential feature, such as the first resist edge 114a, is characterized to a desired extent, for example as measured by a desired number of edge segments. In one embodiment, a potential wafer feature, such as a potential EBR line, is disregarded if edge segments corresponding to a fit curve are only identified across some total percent of the composite image 300. For example, a lower bound could be set that the edge segments associated with a particular fit curve must cumulatively extend across 60%, 80%, or upward to 100% of the composite image. Thus, in some embodiments, an iterative curve fitting process for a particular group of edge segments will continue until the group of concatenated edge segments identified by curve fitting extends across the entire composite image 300.

Additionally, where edge segments have been disregarded from a particular curve fitting operation, for example as being too far from a curve being fit during an iterative process (as determined by another user input or predetermined threshold level, for example), a new curve fitting iteration can begin for fitting a new potential wafer feature line to such disregarded segments. Regardless, several potential wafer feature line candidates optionally result. In some embodiments, the wafer features are resist edges or EBR lines that are chosen from potential EBR line candidates according to their total length, cumulative edge strength, or other factors.

Edge Segment Recycling 340 includes reevaluating edge segments after an initial curve fitting process has been completed. For example, in some embodiments, edge segments which may or may not have previously been incorporated into one of the generated potential wafer feature lines or other edge segment grouping are reprocessed in an effort to further strengthen potential wafer feature identification edge segment candidates. In some embodiments, non-fitted, borderline, and/or fitted edge segments are reviewed and incorporated into one or more edge segment groups according to subsequent curve fitting analysis, such as by reevaluating edge segments according to more forgiving length or edge strength requirements in view of a relatively higher degree of proximity to a particular curve fit, for example.

Figure 10:
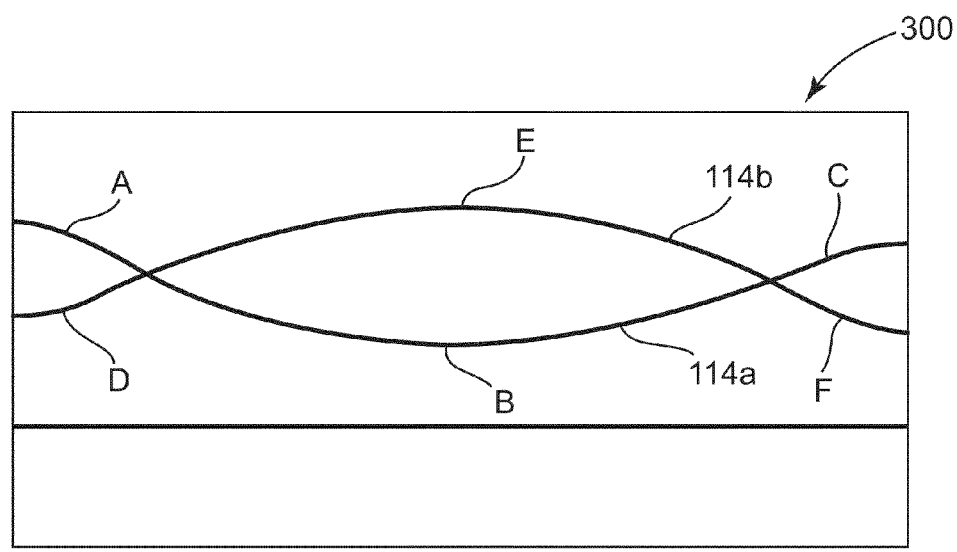
FIG. 10 is a schematic view of a composite image with multiple, crossing, resist edge lines in accordance with principles of the present invention.

With reference to FIG. 10, in some embodiments the above-described methodology is suited for finding multiple, crossing film edge lines, such as EBR lines belonging to separate, distinct resist layers. In particular, FIG. 10 illustrates some embodiments where the resist edge 114a has been found according to groupings of edge segments A, B, C and the resist edge 114b found according to groupings of edge segments D, E, F. With reference to FIG. 10, it should be understood that the sinusoidal curve fitting technique helps ensure that each of the groupings of edge segments A, B, C and the groupings of edge segments D, E, F are associated with each other to identify the resist edges 114a, 114b. In particular, edge segments A, B, C form a highly sinusoidal fit as do edge segments D, E, F, whereas other combinations of the edge segments A, B, C, D, E, F exhibit a lesser degree of sinusoidal fit for evaluating the resist edges 114a, 114b.

In view of the above, it should be understood that information resulting from the edge inspection methodology described above can be used in a variety of applications to identify a variety of wafer features. For example, in some embodiments, EBR location data or other wafer feature data is evaluated and compared against known process tolerances to make a wafer pass/fail decision. In particular, a failed wafer can be stripped and re-worked saving fabrication manufacturing costs. Alternatively, a wafer might be discarded upon failing such inspection.

As previously referenced, several different metrics of various wafer features can be obtained according to some embodiment systems and methods described herein. For example, it should be understood that similar methodology to that described above in association with locating EBR lines is optionally applied to locate the wafer edge 102, the top edge bevel 136, for example, as well as features associated with the bottom edge region 134, features associated with the wafer edge normal 138, and others. As referenced above, the compression process can be used to suppress unwanted edge information or otherwise "bring out" features of interest that extend about the top edge region 100 or other regions. For example, the origin 142 of the top edge bevel 136 can be located at a relatively high degree of accuracy and/or efficiency, which, in combination with the location of the wafer edge 102, can be used to determine mean top edge bevel width, bevel variability, or other metrics as desired. It should clear that similar principles are also applicable to the bottom bevel 140 in view of the foregoing.

Additionally, using a found position of the first resist edge 114a, for example, various other metrics can be evaluated at a relatively high degree of accuracy and/or efficiency. For example, the resist center 112 location can be calculated from the location of the first resist edge 114a. An offset of the resist center 112 from the wafer center 104 can be determined in (R, θ) coordinates and/or (ΔX, ΔY) coordinates as desired. It can also be determined whether the found location of the first resist edge 114a or second resist edge 114b, for example, are within desired tolerance(s). Perimeter information such as minimum and maximum distances from the resist center 112 to the resist edges 114a, 114b, for example, can also be provided. Using the determined resist edges 114a, 114b a roughness measurement for the resist edges 114a, 114b, for example, or standard deviation number representative of how jagged or smooth the resist edges 114a, 114b is can be determined. Additionally, it is contemplated that a basic shape of the resist edges 114a, 114b can be determined (e.g., circular, elliptical, etc.). Where multiple EBR lines are identified, such as resist edges 114a, 114b, "criss-cross" points, or intersections, of the EBR lines can be determined as well as offset between the multiple EBR lines. The above-listed metrics are not meant to be an exclusive list and other potential metrics are also contemplated.

In some embodiments, a "golden EBR" image model or other "golden template" relating to one or more wafer features is created from the compressed, concatenated images. For example, after a statistically significant number of wafers have been inspected and their images compressed, the compressed images are combined into a statistical model with subsequent compressed images being analyzed in light of the model. In some embodiments, image subtraction takes place and the remaining "differences," for example a "difference image," between the "golden template" and the inspection image are optionally analyzed. In some embodiments, such difference images are analyzed to identify defective wafer features or other features that are sufficiently different from the "golden template" image standard.

Additionally or alternatively, defects are optionally identified by setting tolerances for one or more relative measurements (e.g., wafer center position to resist center position, deviation of the identified film layer or other edge from the sinusoidal model, distance of the film layer or other edge from the nominally expected location, and others). For example, in some embodiments, regions of the first resist edge line 114*a* identified as being outside of the tolerance limits are flagged as locally defective. If desired, such "out of spec" regions also cause the entire resist edge line 114*a* to be flagged as defective.

Figure 11:
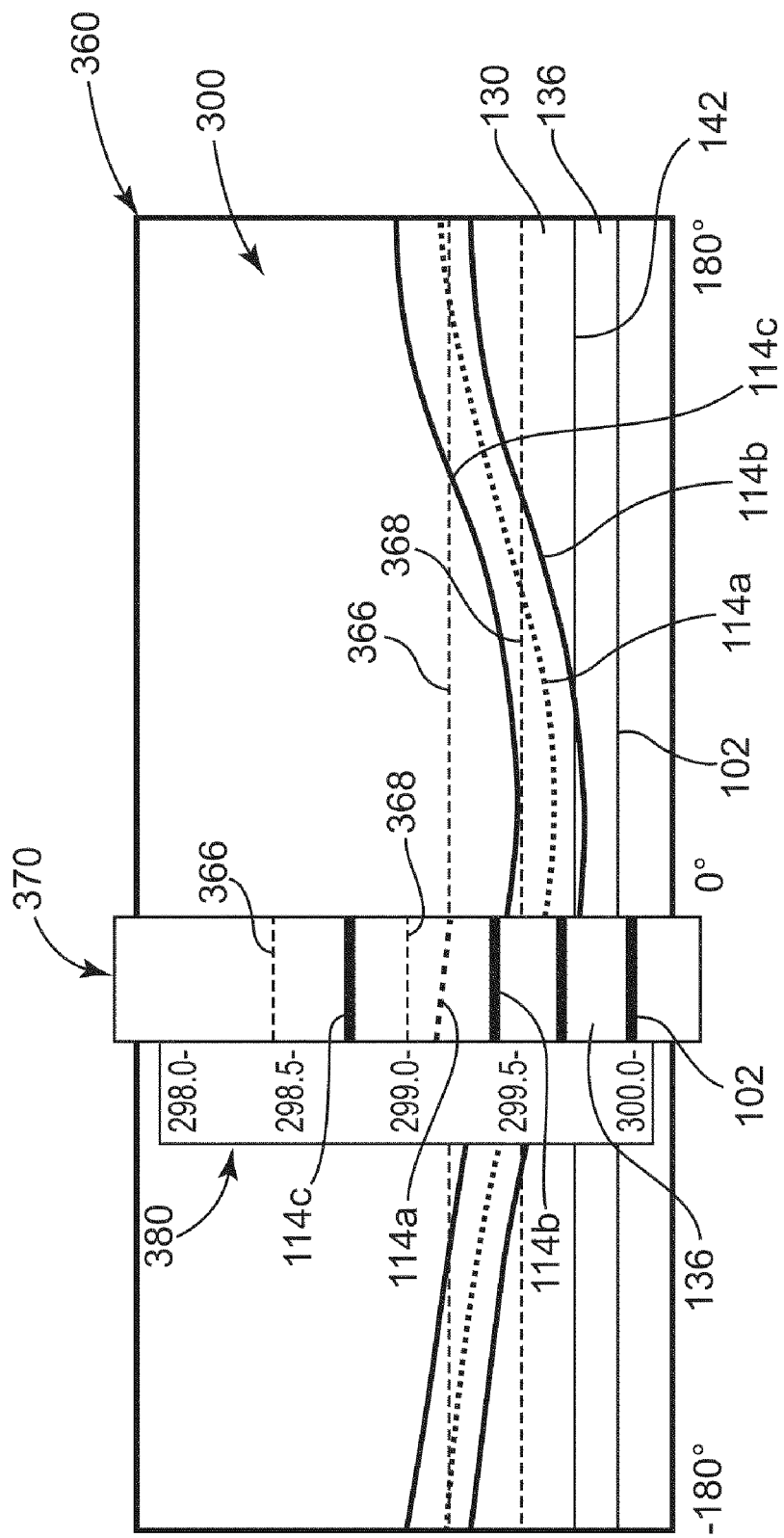
FIG. 11 a schematic view of an embodiment composite image visual display in accordance with principles of the present invention.
Figure 12:
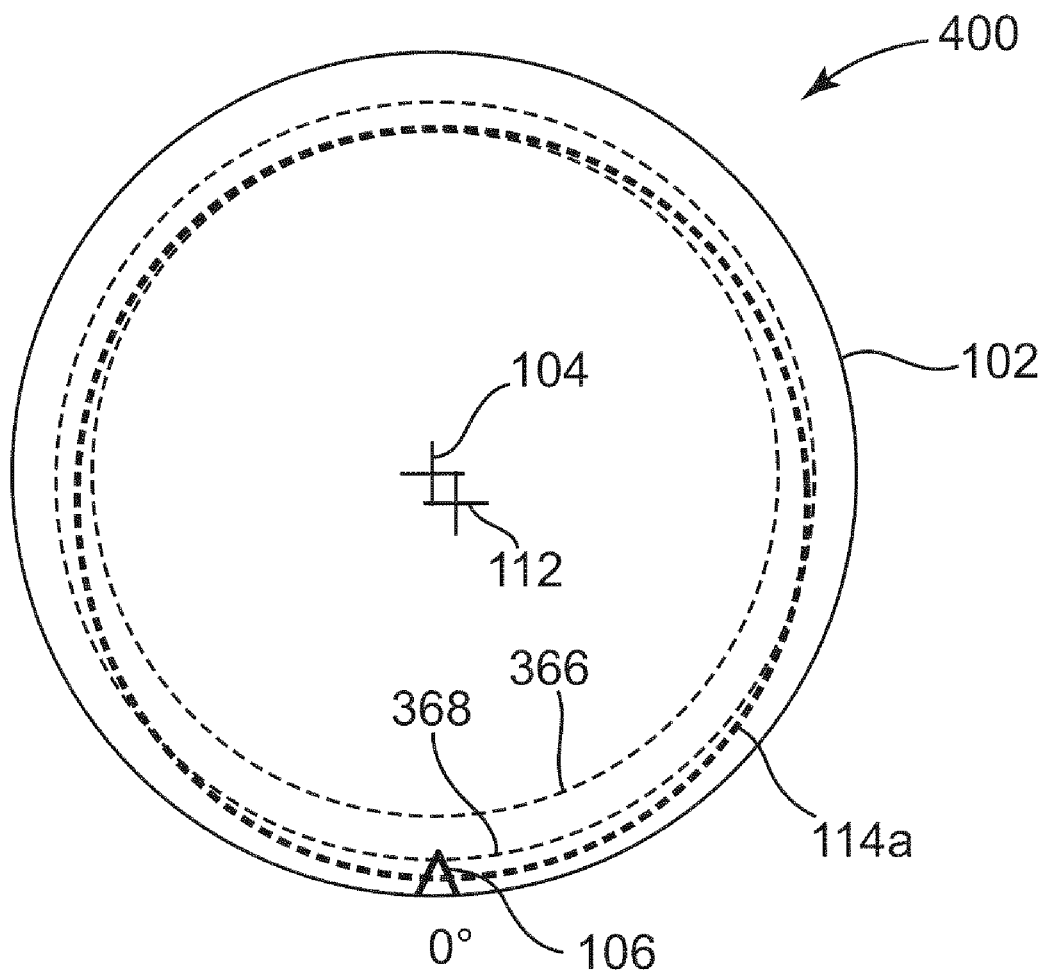
FIG. 12 a schematic view of an embodiment circular map visual display in accordance with principles of the present invention.

With reference to FIG. 11, some embodiments include displaying the composite image 300, including related edge gradient data, edge segment data, or other data as desired, to a user in a composite image visual display 360 (e.g., a computer screen or a print out as appropriate) with visual representations of found wafer features, such as located first resist edge 114*a*, located second resist edge 114*b*, and located third resist edge 114*c* as shown in FIG. 11. With reference to FIG. 11, the composite image 300 is displayed with the found, or identified, first, second, and third resist edges 114*a*, 114*b*, 114*c* displayed as highlighted lines or grouping of edge segments. If desired, a user can select a located wafer feature, such as the first resist edge 114*a*, to further highlight the feature and obtain various metrics associated with the located feature.

Additionally, the composite image visual display 360 may include several controls (not shown) for changing the various thresholds or other criteria applied during Composite Image Data Analysis 240 in order to customize feature detection, for example by selecting different edge thresholding values or minimum edge segment lengths, for example). The found wafer edge 102 and the origin 142 of the top bevel 136 are also optionally displayed as highlighted lines or groupings of edge segments, along with an upper EBR line tolerance 366 and a lower EBR line tolerance 368 for visually evaluating whether a particular EBR line is "out of spec." If desired, various information and metrics can be displayed by numbers, symbols, or text on the composite image visual display 360, e.g., a number of times a selected EBR line passes "out of spec," as well as any of the other metrics previously described, e.g., resist center 112 to wafer center 104 offset, and others.

Additionally, in some embodiments a user is able to select a particular image frame acquisition location on the composite image visual display 360, with a window 370 showing the uncompressed image taken at that frame acquisition location. The found EBR lines, such as the first resist edge 114, wafer edge 102, top bevel 136, and/or the upper and lower tolerances 366, 368 are also optionally displayed in the window 370 showing the uncompressed image. A scale 380 showing relative distance is optionally presented next to the window 370 to provide a user with a frame of reference for relative distances between found or otherwise displayed features. Additionally, in some embodiments, a user is able to select a particular image acquisition frame location for display in the window 370 using a "slider bar" type control or by "clicking and dragging" the window 370 across the composite image visual display 360.

With reference to FIG. 11, a circular map visual display 400 can additionally or alternatively be provided to the composite image visual display 360. The circular map visual display 400 provides a circular representation of the wafer 50 according to the found wafer edge 102. The found first resist edge 114, the inner and outer tolerances 366, 368, and the top edge bevel 136 (not shown in FIG. 11), the wafer notch 106, the resist center 112, and the wafer center 104 are displayed on the circular map display 400 as desired, for example as highlighted lines. It should be understood that any of the information associated with the composite image visual display 360 is also optionally displayed in the circular map visual display 400, and vice versa.

As referenced above, some embodiments of Image Data Acquisition 210, Image Data Compression 220, Image Data Concatenation 230, and Composite Image Data Analysis 240 apply similar data acquisition and analysis techniques to those described above to the bottom edge region 134 and/or the wafer edge normal 138, for example. In particular, some embodiments of Wafer Edge Inspection 200 include acquiring edge normal image data, compressing the edge normal image data, generating a composite image of the compressed edge normal data, and analyzing the composite image, for example, to determine an amount or location of film boundaries on the edge normal 138, layer boundaries, for example silicon and insulator layer boundaries and their relative thicknesses, or other wafer features. With reference to particular edge films, prior to resist layers or other films being removed from the exposed edge region 130, such films can cover part of the wafer edge normal 138 to an unacceptable extent, which interferes with subsequent processing. As such, a method of identifying boundaries of such films can be desirable.

Similarly, some embodiments of Image Data Acquisition 210, Image Data Compression 220, Image Data Concatenation 230, and Composite Image Data Analysis 240 include analyzing the bottom edge region 134. In particular, some embodiments of Wafer Edge Inspection 200 include acquiring edge bottom image data, compressing the edge bottom image data, generating a composite image of the compressed edge bottom data, and analyzing of the composite image, for example, to identify features associated with the bottom edge region 134.

Although specific embodiments have been illustrated and described herein, it will be appreciated by those of ordinary skill in the art that a wide variety of alternate and/or equivalent implementations calculated to achieve the same purposes may be substituted for the specific embodiments shown and described without departing from the scope of the present invention. Those with skill in the chemical, mechanical, electro-mechanical, electrical, and computer arts will readily appreciate that the present invention may be implemented in a very wide variety of embodiments. This application is intended to cover any adaptations or variations of the preferred embodiments discussed herein. Therefore, it is manifestly intended that this invention be limited only by the claims and the equivalents thereof.

Although the present invention has been described with reference to preferred embodiments, workers skilled in the art will recognize that changes can be made in form and detail without departing from the spirit and scope of the present invention.

What is claimed is:

1. A wafer edge inspection method, comprising:
   acquiring a plurality of images about an edge portion of a wafer, each of the images comprising an array of pixels having a first dimension and a second dimension, each pixel of the array of pixels having a characteristic pixel value;
   compressing each array of pixels across the first dimension to generate a plurality of compressed pixel arrays;
   analyzing the plurality of compressed pixel arrays to generate a plurality of edge segments;
   evaluating a wafer feature by identifying edge segments of the plurality of edge segments that correspond to the wafer feature using a sinusoidal line fitting operation; and
   modifying a wafer processing step based on the analysis of the plurality of compressed pixel arrays.

2. The method of claim 1, wherein the edge portion of the wafer is an annular region extending circumferentially about the wafer, the annular region defined by an inner diameter inside of an exposed region of the wafer characterized as being substantially free of resist and an outer diameter outside of the edge of the wafer.

3. The method of claim 1, wherein analyzing the plurality of compressed pixel arrays to identify the plurality of edge segments comprises:
    applying an edge detector to the plurality of compressed pixel arrays to generate edge gradient data; and
    performing edge analysis on the edge gradient data to generate edge segment data corresponding to the plurality of edge segments.

4. The method of claim 1, wherein analyzing the plurality of compressed pixel arrays to identify the plurality of edge segments further comprises:
    filtering the edge segment data according to at least one of edge segment edge strength and edge segment length.

5. The method of claim 1, wherein the wafer feature is a first edge bead removal (EBR) line and evaluating the wafer feature includes locating the edge bead removal (EBR) line, the method further comprising:
    locating a second edge bead removal (EBR) line using the composite image; and
    identifying one or more potential crossing points between the located first edge bead removal (EBR) line and the located second edge bead removal (EBR) line.

6. The method of claim 1, wherein the wafer feature is a film edge of a layer of film deposited on the wafer, the method further comprising:
    providing one or more tolerances for the film edge; and
    evaluating whether the film edge is at a desired distance from the wafer edge.

7. The method of claim 1, further comprising:
    selecting a regular wafer feature to be removed from analysis; and
    disregarding image data corresponding to the regular wafer feature.

* * * * *